United States Patent [19]

Ricca

[11] Patent Number: 5,616,810
[45] Date of Patent: Apr. 1, 1997

[54] PROCESS FOR THE PREPARATION OF DEACTIVATED ANILINES

[75] Inventor: Jean-Marc Ricca, Lyon, France

[73] Assignee: Rhone-Poulenc Chimie, Courbevoie, France

[21] Appl. No.: 412,653

[22] Filed: Mar. 28, 1995

Related U.S. Application Data

[62] Division of Ser. No. 156,633, Nov. 24, 1993, Pat. No. 5,401,882.

[30] Foreign Application Priority Data

| Nov. 25, 1992 | [FR] | France | 92 14160 |
| Nov. 25, 1992 | [FR] | France | 92 14157 |
| Nov. 28, 1992 | [FR] | France | 92 14155 |

[51] Int. Cl.⁶ ........................ C07C 209/64; C07C 209/62
[52] U.S. Cl. .................. 564/442; 560/19; 560/45; 560/47; 564/395; 564/405; 564/427; 564/428; 564/441
[58] Field of Search ........................ 564/442, 441

[56] References Cited

U.S. PATENT DOCUMENTS

| 2,887,514 | 5/1959 | Schmerling et al. | 564/406 |
| 4,292,446 | 9/1981 | Riley | 564/414 |
| 5,025,107 | 6/1991 | Chamberlin | 564/414 |

FOREIGN PATENT DOCUMENTS

| 197707 | 7/1977 | U.S.S.R. | 564/414 |

*Primary Examiner*—Peter O'Sullivan
*Attorney, Agent, or Firm*—Finnegan, Henderson, Farabow, Garrett & Dunner, L.L.P.

[57] ABSTRACT

The present invention is directed to a process for the preparation of deactivated anilines, which comprises the step of reacting a compound of formula (I)

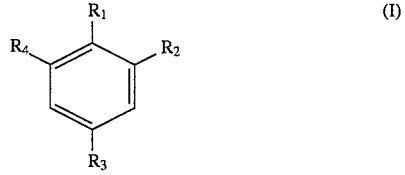

(I)

with a dialkylamide in the presence of a base at elevated temperature, in which:

$R_1$ is chosen from groups whose anions ($R_1^-$) constitute leaving groups;

$R_2$ and $R_4$, which may be the same or different, are chosen from hydrogen, hydrocarbon chains, halogens and groups which are electron-attracting (EAG);

$R_3$ is chosen from hydrocarbon chains, halogens and groups which are electron-attracting, preferably through an inductive effect rather than a mesomeric effect;

with the proviso that at least one of the groups $R_2$, $R_3$, and $R_4$ is electron-attracting through an inductive effect.

A second embodiment of the present invention is directed to a process for the dealkylation of deactivated anilines which comprises the steps of free radical halogenation of the benzyl carbon followed by hydrogenation. A third embodiment of the present invention is directed to a process for the dealkylation of deactivated anilines which comprises the step of reacting an alkylated aniline with an amine in the presence of a catalytic amount of a pyridine salt.

A fourth embodiment of the present invention is direct to intermediates for the preparation of deactivated anilines which have the formula (III)

$$Ar-N(-CH_{2-x}Z_x-R_1')(-CH_{2-y}Z_y-R_2')$$ (III)

wherein

Z represents a halogen atom;

$R_1'$ and $R_2'$, which may be the same or different, are each a hydrogen atom or an alkyl radical having at most 4 carbons;

x and y, which may be the same or different, are each an integer of 0 or 1, with the proviso that x+y is at least equal to 1; and Ar is a deactivated aromatic ring, preferably derived from formula (I) by replacement of $R_1$ with a dialkylamine.

19 Claims, No Drawings

PROCESS FOR THE PREPARATION OF DEACTIVATED ANILINES

This is a division of application Ser. No. 08/156,633, filed Nov. 24, 1993, now U.S. Pat. No. 5,401,882.

The present invention is directed to processes for the synthesis of deactivated anilines. The present invention is also directed to a process of grafting a monoalkylamine or dialkylamine onto a deactivated aromatic ring. The present invention is further directed to a process for the dealkylation of deactivated anilines and novel intermediate compounds useful for the preparation of deactivated anilines.

The synthesis of anilines has generally been performed by hydrogenation of aromatic nitro compounds. This technique, however, is subject to a large number of constraints which limit its practical usefulness. For example, hydrogenation is not appropriate when other substituents, or even the reaction products, are sensitive to hydrogenolysis. Nor is hydrogenation appropriate when it gives rise to a large number of side reactions.

Moreover, the positioning of the nitro function on the aromatic ring may be difficult, necessitating a complex multistep synthesis and the use of expensive reagents. Accordingly, there is a need for a direct and facile method for the preparation of deactivated anilines.

With respect to the dealkylation of deactivated anilines, the usual method for demethylating anilines employs aqueous hydrobromic acid (HBr), the use of which runs the risk of destroying other functional groups which may be present on the ring. Such functional groups whose lability is well-known include halogenated groups, in particular groups which are perhalogenated at the benzyl position, such as trifluoromethyl. There is, therefore, a need for a simple and effective process for dealkylating deactivated anilines.

As used herein, the term "deactivated aniline" is intended to denote any amine linked directly to an electron-depleted aromatic ring-system such that the associated acid possesses a pKa no greater than 2, preferably no greater than 1. Thus, aniline should be understood to include not only aniline itself, but also the chemical compounds originating from the substitution of aniline, including anilines associated with other ring-system(s), for example, naphthylamines. The electron depletion of the ring-system may be due to any cause known to those skilled in the art, such as the presence of electron-attracting group(s) ("EAG"), which are also known as electron withdrawing groups, or the presence of a hetero atom in one of the rings of a multi-ring system.

SUMMARY OF THE INVENTION

In a first embodiment, the present invention is directed to a process for the preparation of deactivated anilines, which comprises the step of reacting a compound of formula (I)

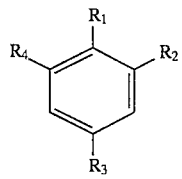
(I)

with a dialkylamide in the presence of a base at elevated temperature, in which:

$R_1$ is chosen from groups whose anions ($R_1^-$) constitute leaving groups;

$R_2$ and $R_4$, which may be the same or different, are chosen from hydrogen, hydrocarbon chains, halogens and groups which are electron-attracting (EAG);

$R_3$ is chosen from hydrocarbon chains, halogens and groups which are electron-attracting, preferably through an inductive effect rather than a mesomeric effect;

with the proviso that at least one of the groups $R_2$, $R_3$, and $R_4$ is electron-attracting through an inductive effect.

A second embodiment of the present invention is directed to a process for the dealkylation of deactivated anilines which comprises the steps of free radical halogenation of the benzyl carbon followed by hydrogenation.

A third embodiment of the present invention is directed to a process for the dealkylation of deactivated anilines which comprises the step of reacting an alkylated aniline with an amine in the presence of a catalytic amount of a pyridine salt.

A fourth embodiment of the present invention is direct to intermediates for the preparation of deactivated anilines which have the formula (III)

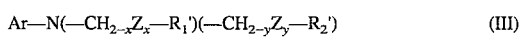

$$Ar-N(-CH_{2-x}Z_x-R_1')(-CH_{2-y}Z_y-R_2') \qquad (III)$$

wherein

Z represents a halogen atom;

$R_1'$ and $R_2'$, which may be the same or different, are each a hydrogen atom or an alkyl radical having at most 4 carbons;

x and y, which may be the same or different, are each an integer of 0 or 1, with the proviso that x+y is at least equal to 1; and Ar is a deactivated aromatic ring, preferably derived from formula (I) by replacement of $R_1$ with a dialkylamine.

DETAILED DESCRIPTION OF THE PREFERRED EMBODIMENTS

A first embodiment of the present invention is directed to a process for the preparation of deactivated anilines, which comprises the step of reacting a compound of formula (I)

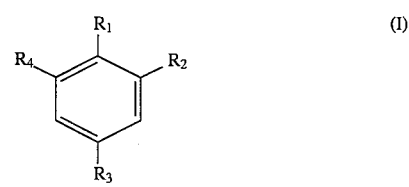
(I)

with a dialkylamide in the presence of a base at elevated temperature, in which:

$R_1$ is chosen from groups whose anions ($R_1^-$) constitute leaving groups;

$R_2$ and $R_4$, which may be the same or different, are chosen from hydrogen, hydrocarbon chains, halogens and groups which are electron-attracting (EAG);

$R_3$ is chosen from hydrocarbon chains, halogens and groups which are electron-attracting, preferably through an inductive effect rather than a mesomeric effect;

with the proviso that at least one of the groups $R_2$, $R_3$, and $R_4$ is electron-attracting through an inductive effect.

Optionally, the aromatic ring may also be substituted at one or both of the positions meta to $R_1$. If substituted, the substituents are preferably groups which exert at least as much electron attraction through an inductive effect as alkyl groups, such as halogen atoms and pseudohalogens. The substituent(s), however, must be of an appropriate size so as not to sterically hinder the reaction.

$R_1$ may be any functional group whose anion is a leaving group, preferably a good leaving group; as used herein, the term "good leaving group" refers to those moieties for which the acid associated with the anion possesses a pKa value no greater than 1. Preferably, $R_1$ is a group for which the acid associated with the anion has a pKa no greater than 0; more preferably, the pKa of the acid is no greater than −1. Preferably, $R_1$ is a halogen atom, such as bromine or chlorine. Most preferably, $R_1$ is chlorine.

Preferably, either as a result of the nature of the functional group or as a result of the arrangement of EAG's on the aromatic ring, the anions $R_1^-$ constitute better leaving groups than anions derived from the radicals $R_2$ to $R_4$.

$R_2$ and $R_4$, which may be the same or different, are each chosen from hydrogen, hydrocarbon chains, halogens and EAG's. Preferably, the EAG's attract electrons through an inductive effect, as opposed to a mesomeric, or resonance, effect. Suitable EAG's include pseudohalogens, alkoxycarbonyl groups, halogen atoms such as fluorine, chlorine and bromine, and perhaloalkyl groups. Of the halogen atoms, chlorine is a preferred EAG.

As used herein, the term "pseudohalogen" is intended to mean radicals capable of forming an anionic leaving group for which the acid associated with the anion has a pKa of no greater than 1. Preferably, the acid associated with the anion has a pKa no greater than 0; more preferably, no greater than −1.

Preferably, the EAG's are perhaloalkyl groups. More preferably, the EAG's are trihalomethyl groups; most preferably, the EAG's are trifluoromethyl groups. As used herein, the term "perhaloalkyl" is intended to mean groups having the formula

$$R-(CX_2)_n-$$

wherein n is equal to at least 1 and, where R is not an electron-attracting group, preferably equal to 2, each X is, independently, a halogen atom, preferably fluorine or chlorine, and R is a $C_1$ to $C_{10}$ hydrocarbon, alkyl or aryl residue, or a halogen atom.

If a hydrocarbon, R preferably has from 1 to 6 carbon atoms, more preferably, from 1 to 4 carbon atoms. Most preferably, R is an EAG, such as halogen atom.

The groups X are most often identical. Generally, n is an integer of not more than 10. Preferably, when the perfluoroalkyl group is at the ortho position, n is an integer less than 6 and more preferably less than 4. The perhaloalkyl group must be of an appropriate size so as not to sterically hinder the reaction.

$R_3$ is chosen from hydrogen, hydrocarbon chains, halogens and EAG's which are electron-attracting through an inductive effect but not a mesomeric effect.

Optionally, $R_2$ and/or $R_4$ may, together with the substituent at the respective adjacent position meta to $R_1$, form at least one additional aromatic ring, such as a naphthalene, anthracene, phenanthrene or chrysene ring system. The additional aromatic ring(s) may, of course, be substituted.

Among suitable bases which can be used in the inventive process, anionic bases are preferred, such as carbonates. Preferably, the base is chosen from among alkali metal oxides, alkali metals amides and alkali metal hydroxides and alcoholares. Preferably, the pKa of the conjugate acid of the base employed is at least equal to 9, more preferably 10, and most preferably 12. For economic reasons, sodium hydroxide is a particularly preferred base.

The amide used in the inventive process is preferably a dialkylamide of a carboxylic acid. More preferably, the amide is a dialkylamide of a carboxylic acid having not more than 10 carbon atoms. It is also possible to use dialkylamides such as tetramethylureas and tetramethylguanidines. Preferably, the dialkylamides are dialkylformamides. Preferably, the dialkylformamides are such that the number of carbon atoms in the alkyl radicals grafted to the nitrogen is not more than 6. More preferably, the number of carbon atoms is not more than 4 and most preferably not more than 3. Methyl derivatives are the particularly preferred derivatives.

The reaction of a dialkylamide and a compound having formula I preferably takes place at a temperature of between 150° and 300° C., and more preferably between 180° and 250° C.

The solvent employed in the present process can be any solvent or mixture of solvents which does not decompose under reaction conditions and is inert with respect to the reactants. Preferably the solvent is polar, i.e., has a dielectric constant ε equal to at least 30. When the solvent is protic, the solvent should possess a pKa preferably at least equal to 14, the pKa of water. When there is a single solvent, it is preferable to use either an excess of reactants or an excess of substrate.

It should be noted that the reaction system tolerates hydroxylated derivatives, such as water, as solvents, particularly when a copper compound is used as a catalyst for the reaction. Thus, in a preferred embodiment, the reaction is carried out in the presence of from 0.1 mol% to 1.0 mol% of a cuprous salt relative to the substrate. Examples of suitable cuprous salts are cuprous chloride and cuprous acetate.

Preferably, the amounts of reactants and catalysts introduced are as follows, taking as reference the quantity of the compound of formula I equal to 1:

base: from 0.5 to 5 gram-equivalents, preferably from 2 to 4 gram-equivalents; and amide: 1 to 100 gram-equivalents, preferably from 5 to 25 gram-equivalents.

The reaction takes place in an autoclave at the normal pressure of the reactants under the experimental conditions. Although not essential, it is preferred that the reaction take place in an inert atmosphere, for example, under nitrogen or under argon.

According to the present invention, it has been possible to prepare para-trifluoromethyl-N,N-dimethylanilines in a single step from the corresponding halogenated derivatives. The results observed are generally better when the starting material is a dihalogenated or trihalogenated derivative at the meta and para positions of a perfluoroalkyl electron-attracting function.

Preferably, there are no more than four substituents on the aromatic ring. In such an embodiment of the present invention, $R_1$ is chlorine or bromine, preferably chlorine; $R_2$ is fluorine, chlorine or bromine, preferably chlorine; the position meta to $R_1$ is hydrogen, fluorine, chlorine or bromine, preferably chlorine; and $R_3$ is perfluoroalkyl, in general trifluoromethyl.

However, the tertiary aniline compounds obtained by this embodiment of the present invention may not all be useful directly; the primary or the secondary aniline may, in certain applications, be even more useful than the corresponding tertiary aniline.

Accordingly, a second embodiment of the present invention is directed to a process for the dealkylation of deactivated anilines, which comprises free radical halogenation of an alkylated deactivated aniline followed by hydrolysis of the halogenated product. Preferably, the deactivated aniline has the formula II

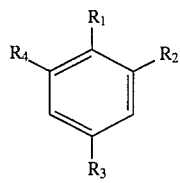 (II)

in which $R_1$ represents a mono- or dialkylamino radical and $R_2$ through $R_4$ are as defined above. Additionally, the positions meta to $R_1$ may optionally be substituted as before.

The free radical halogenation is carried out under conditions which are generally known to those skilled in the art, preferably conditions involving initiation of the reaction by electromagnetic radiation of suitable wavelength, peroxides or other equivalent initiators.

The halogenating agent is preferably the molecular or atomic halogen. Alternatively, the halogenating agent may be any compound known to those skilled in the art which can generate a halogen free radical. Such compounds include thionyl or sulfuryl halides, such as thionyl chloride, phosphorous pentachloride, mixtures of $PCl_3/Cl_2$, alkyl hypochlorites and compounds of the type $X_2O$, in which X is a halogen other than fluorine or iodine. In the case of bromine, mention should be made, when they are stable and not too toxic, of the compounds corresponding to the above chlorine compounds, as well as compounds of the N-bromosuccinimide (NBS) type. In the case of iodine, the best iodinating agent remains molecular iodine.

In a first stage of the free radical halogenation, if either $R_2$ or $R_4$ are hydrogen, these positions are halogenated by the free radical halogenating agent. In a second stage, one or both of the alkyl groups is monohalogenated at the α position to give compounds having the formula III:

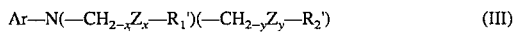 (III)

Z represents a halogen atom;

$R_1'$ and $R_2'$, which may be the same or different, are each a hydrogen atom or an alkyl radical having at most 4 carbons;

x and y, which may be the same or different, are each an integer of 0 or 1, with the proviso that x+y is at least equal to 1; and Ar is a deactivated aromatic ring, preferably derived from formula (I) by replacement of $R_1$ with a dialkylamine; it being possible for $R_1'$ and $R_2'$ to be linked to make just a single radical forming a ring with the nitrogen. Preferably, $R_1'$ and $R_2'$ are each a hydrogen atom.

If the amount of halogenating agent is limited to the stoichiometric amount, or to an approximately 10% excess relative to the stoichiometry for a single dealkylation, only one alkyl group is halogenated. If the amount of the halogenating agent is not limited, both alkyl groups will be halogenated at the benzyl position. The choice of the stoichiometry therefore makes it possible to choose between a halogenation of the ring, a monodealkylation or a didealkylation.

The inventive dealkylation is especially surprising with respect to its selectivity, since the meta positions are not affected and the carbons of the alkyl chains situated at the α position with respect to the aniline function are not substantially affected more than once, thereby making it possible to economize on expensive reactants and reducing the amounts of effluents. It is even possible to effect a selective monodealkylation of the aniline (in the broad sense of the term).

During the study which led to the present invention, it was shown that this halogenation involves only the alkyl carbons linked directly to the aniline function, and, if they are hydrogen atoms, the ortho and para substituents, or equivalent substituents, on the aromatic ring(s).

In general, this free radical halogenation step preferably takes place at a temperature of between 0° and 100° C., and more preferably in the region of a point between 0° C. and 50° C.

Preferably, the halogenation occurs in chlorinated or simply polar solvents. When solvents are used whose boiling point is below 100° C., it is practical to work at the reflux temperature. Thus, where appropriate, it is practical to work under reduced pressure to bring the refluxing temperature to within the preferred range.

The free radical halogenation can introduce various halogens such as from chlorine, bromine or iodine into the molecule. In general, on economic grounds, chlorine is preferred. However, when it is desired to supply a specific halogen to the ring, it is appropriate to use a halogenating agent that supplies this halogen.

The same considerations apply when it is desired to avoid a perhalogenation of free ortho and para positions, or equivalent positions, with respect to the aniline; in this case, halogenation is performed with an agent that introduces a halogen of higher rank than those present in the ring, and dehydrohalogenation is then carried out by means that are known to those skilled in the art to be selective.

Any solvents which are inert under the reaction conditions may be used for the free radical halogenation. Such solvents include carbon tetrachloride, chlorobenzene, dichlorobenzene and acetonitrile.

When the reactants are not naturally free-radical reactants, e.g., thionyl or sulfuryl chlorides, they are preferably employed in the presence of an agent or conditions promoting free-radical formation. Preferably, the agent is actinic radiation, which is known to those skilled in the art to promote the formation of Hal·.

Procedures for the hydrolysis of the compounds of formula III is generally known to those skilled in the art, and are preferably carried out in the presence of an absorber of the acids released.

Unexpectedly, the intermediate products of formula

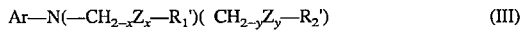 (III)

are sufficiently stable to be able to be isolated, and constitute precursors of a large number of chemical derivatives. These compounds represent a fourth embodiment of the present invention. Preferably, Z is a chlorine atom, x=1 and y=1.

In addition, the isolation of these compounds from the reaction medium enables a better purity of the totally or partially dealkylated aniline to be obtained; the separation is greatly facilitated by the fact that the compounds in which y=1 and x=1 are greatly preponderant in the reaction mixture.

As noted above, the halogenation-hydrolysis process for dealkylation of alkylanilines may result in halogenation of the ortho positions of the parent alkylaniline. Accordingly, as an alternative, a third embodiment of the present invention is directed to a process for dealkylation of deactivated alkylanilines without affecting the initial aromatic radical, which comprises reacting the aniline with ammonia or a primary or secondary amine, in free form or the form of one of its salts, in the presence of a catalytic amount of a pyridine salt.

This surprising reaction possesses the advantage, for dialkylanilines, of being selective and of being possible even when the alkylanilines are secondary.

As used herein, the term "amine" should be understood to include a mixture of the amines defined above. The amine can also be a pyridine or substituted pyridine. As salts, amine hydrohalides, particularly amine hydrochlorides, are preferred.

As used herein, "pyridine" is intended to mean any compound possessing a pyridine ring in which the nitrogen atom does not possess a substituent. Thus, pyridine should be understood to include not only pyridine itself, but also the chemical compounds originating from the substitution of pyridine, including pyridines associated with other ring-system(s), for example, quinoline. It is preferable for the substitutes for pyridine itself to possess a boiling point equal to not more than approximately 200° C. Naturally, "pyridine" should also be understood to include a mixture of the pyridines defined above. Preferably, the pyridine employed is a pyridine hydrohalide salt, most preferably, pyridine hydrochloride, either alone or in the presence of the amine hydrochloride.

As with the halogenation-hydrolysis process, it is also possible with this method to carry out a mono- or a didealkylation. In particular, there is monodealkylation when the acid corresponding to the pyridine salt and/or to the amine salt is a relatively weak acid, i.e., one whose pKa is no less than 1, preferably no less than 3.

Preferably, the amine possess a pKa which is greater than that of the pyridine, preferably by at least two units and more preferably by two and a half units.

Preferably, the process of dealkylation according to this third embodiment of the invention is carried out at a temperature of from 150° to 250° C.; more preferably from 180° to 220° C. It is preferred that an excess of between 1 and 50 equivalents of amine be employed, more preferably between 2 and 10 equivalents, relative to the stoichiometry of the demethylation. In a preferred embodiment, an excess of amine is employed along with an excess of pyridine, preferably pyridine hydrochloride.

One of the most surprising and most advantageous aspects of this technique is that no lysis by ammonia or amine is observed, even in the case where the aniline possesses a perfluoroalkyl group.

The dealkylation reaction is facilitated by the pKa of the acid associated with the aniline being no greater than 5. Preferably, the pKa of the corresponding acid is no greater than 2, more preferably no greater than 1, and most preferably no greater than 0.

The following examples are merely illustrative of the invention and should not be construed as limiting. One skilled in the art can make, without undue experimentation, various substitutions and variations and by equivalent means, performing in substantially the same manner, obtain substantially the same results without departing from the teaching and spirit of the invention.

TYPICAL EXAMPLES

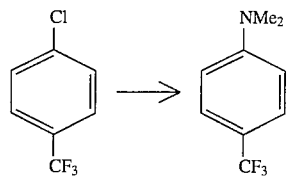

p-Chlorotrifluoromethylbenzene (1.29 g, 7.15 mmol) of DMF (4 g) and sodium amide (0.56 g, 14.3 mol) were introduced in order into a (100 ml) jacketed Teflon autoclave.

The autoclave was closed and the mixture was heated with stirring to 180° C. for 24 h. After treatment of the reaction medium, para-trifluoromethyl-N,N-dimethylaniline was obtained (DC 74%, TY 77%).

---

*Influence of the solvent:

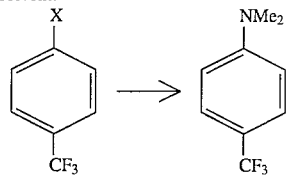

X = Br or preferably Cl
Conditions: CF$_3$-Φ-Cl 0.322 g (1.79 mmol)
NaNH$_2$ 0.14 g (53.6 mmol)
DMF 4 g
(100 ml) jacketed Teflon autoclave.

| Solvent | 0° (C.) | t (H) | AY | DC | CY |
|---|---|---|---|---|---|
| Example No. 1 DMF | 210 | 24 | 57 | 82 | 70 |
| Example No. 2 Dimethylacetamide | 220 | 24 | 30 | 76 | 37 |
| Example No. 3 Tetramethylurea | 200 | 24 | 32 | 65 | 50 |
| Example No. 4 Tetramethylguanidine | 210 | 24 | 30 | 96 | 32 |

° Temperature range: 150–230° C. with DMF.

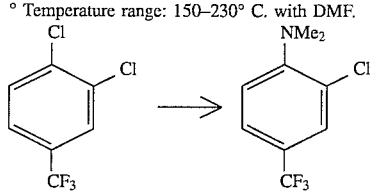

A 1-liter Hastelloy™ autoclave was charged with 3,4-dichlorotrifluoromethylbenzene (47.1 g, 0.212 mol), DMF (200 g) and sodium hydroxide pellets (25.8 g, 0.645 mol).

The autoclave was closed and the mixture was heated with stirring to 210° C. for 3 hours. The pressure reached 9 bars.

After treatment of the reaction medium, 4-trifluoromethyl-2-chloro-N,N-dimethylaniline was obtained (DC 92%)(CY 93%).

| *Parameter | Example No. 5 | Example No. 6 | Example No. 7 | Example No. 8 | Example No. 9 |
|---|---|---|---|---|---|
| 3,4-Dichloro-trifluoromethyl-benzene | 0.215 | 0.225 | 0.225 | 0.222 | 0.224 |
| (mmol) | 1 | 1 | 1 | 1 | 1 |
| DMF (g) | 4 | 4 | 4 | 4 | 4 |
| (equiv.) | 55 | 55 | 55 | 55 | 55 |
| NaOH (g) | — | — | 0.044 | 0.048 | — |
| (equiv.) | — | — | 1.1 | 1.2 | — |
| $H_2O$ (g) | 0.210 | 0.211 | — | — | — |
| (equiv.) | 12 | 12 | — | — | — |
| NaOH 37% (g) | — | — | — | — | 0.202 |
| (equiv) | — | — | — | — | 1.8 NaOH 7 $H_2O$ |
| θ (= °C.) | 195 | 195 | 195 | 195 | 195 |
| T (hours) | 20 | 20 | 20 | 20 | 20 |
| DC (%) | 45 | 75 | 59 | 78 | 91 |
| CY (%) | 87 | 86 | 71 | 67 | 64 |

EXAMPLE NO. 10

Sulfuryl chloride (9.5 g, 70 mmol) was added to a solution of 2-chloro-4-trifluoromethyl-N,N-dimethylaniline (14.25 g, 63.8 mmol) in carbon tetrachloride (90 ml).

The experiment was carried out in the presence of a strong lamp and in the absence of light. After heating to 70° C. for 2 hours, the solution was treated with an excess of 50% sodium hydroxide in water.

HPLC analysis of the organic phase showed the following results:

| Conditions | 2,6-dichloro-4-trifluoromethyl-N-N-dimethylaniline | 2,6-dichloro-4-trifluoromethyl-N-methylaniline |
|---|---|---|
| In presence of lamp | 5–10% | 85% |
| In daylight | 68% | 17% |
| In darkness | 90% | 0% |

EXAMPLE NO. 11

A mixture of 2,6-dichloro-4-trifluoromethyl-N,N-dimethylaniline (4.5 g, 17.4 mmol) and 2,6-dichloro-4-trifluoromethyl-Nmethylaniline (1.88 g, 6.9 mmol) dissolved in carbon tetrachloride (60 ml) was treated with sulfuryl chloride (5.7 g, 42.2 mmol).

The reaction mixture, cooled to 10° C. was illuminated by means of a UV lamp for 6 hours, and then treated with an excess of 50% sodium hydroxide in water. HPLC analysis of the organic phase showed the presence of 2,6-dichloro-4-trifluoromethylaniline (70 mol%).

EXAMPLE NO. 12

2,6-Dichloro-4-trifluoromethyl-N-methylaniline (1.318 g, 5.4 mmol) dissolved in carbon tetrachloride (40 ml) was treated with sulfuryl chloride (4.5 g, 33 mmol). The reaction mixture, cooled to 10° C., was illuminated by means of a lamp for one hour, and then treated with an excess of 50% sodium hydroxide in water. HPLC analysis of the organic showed the presence of 2,6-dichloro-4-trifluoromethylaniline (83 mol%).

EXAMPLE 13

A theoretical amount of gaseous chlorine was introduced into a solution of 2,6-dichloro-4-trifluoromethyl-N,N-dimethylaniline (3 g, 11.6 mmol) in carbon tetrachloride (60 ml).

During the introduction of chlorine, the reaction mixture was cooled to 10° C. and illuminated by means of a UV lamp. HPLC analysis of the organic phase after treatment showed, after 1 hour, a 92% conversion and a 64% yield of 2,6-dichloro-4-trifluoromethylaniline.

EXAMPLE NO. 14

A theoretical amount of gaseous chlorine was introduced into a solution of 2,6-dichloro-4-trifluoromethyl-N,N-dimethylaniline (2.25 g, 8.7 mmol) in 1,2-dichlorobenzene (65 ml).

During the introduction of chlorine, the reaction mixture was cooled to 10° C. and illuminated by means of a UV lamp.

HPLC analysis of the organic phase after treatment showed, at the end of 50 minutes, a 99% conversion and a 92% yield of 2,6-dichloro-4-trifluoromethylaniline.

EXAMPLE NO. 15

A theoretical amount of gaseous chlorine was introduced into a solution, cooled to 10° C., of 2,6-dichloro-4-trifluoromethylaniline (8.45 mmol) in 1.2 dichlorobenzene (65 ml). After illumination of the reaction mass by means of a UV lamp for 15 minutes, the reaction was continued and protected from light for 2 hours. HPLC analysis of the organic phase after treatment showed a 98% conversion and a 34% yield of 2,6-dichloro-4-trifluoromethylaniline.

EXAMPLE NO. 16

1,2,3,-Trichlorobenzene (0.963 g), DMF (4 g) and sodium hydroxide (0.4 g) were introduced in order into a (100 ml) jacketed Teflon autoclave.

The autoclave was closed and the mixture was heated with stirring to 220° C. for 24 hours. The conversion was then 78%.

After treatment of the reaction medium, 0.517 g of the mixture of N,N-dichlorodimethylanilines was brought into contact with pyridine hydrochloride (5.70 g).

The mixture was heated to 185° C. for 45 minutes.

HPLC analysis of the mixture showed the presence of 2,3-dichloroaniline (95%) and of 2,6-dichloroaniline (5%).

EXAMPLE NO. 17

1,2,4-Trichlorobenzene (0.766 g), DMF (4 g) and sodium hydroxide (0.4 g) were introduced in order into a (100 ml) jacketed Teflon autoclave.

The autoclave was closed and the mixture was heated with stirring to 220° C. for 24 hours. The conversion was then 82%.

After treatment of the reaction medium, 0.223 g of the mixture of chloro-N,N-dimethylanilines was brought into contact with pyridine hydrochloride (3.2 g).

The mixture was heated to 185° C. for 60 minutes.

HPLC analysis of the mixture showed the presence of 2,4-dichloroaniline (96%) and of 3,4-dichloroaniline (4%).

EXAMPLE NO. 18

1,2,4,5-Tetrachlorobenzene (0.919 g), DMF (4 g) and sodium hydroxide (0.4 g) were introduced in order into a (100 ml) jacketed Teflon autoclave.

The autoclave was closed and the mixture was heated with stirring to 220° C. for 24 hours. The conversion was then 100%.

After treatment of the reaction medium, 0.50 g of the mixture of trichloro-N,N-dimethylanilines was brought into contact with pyridine hydrochloride (5.8 g).

The mixture was heated to 190° C. for 60 minutes.

HPLC analysis showed the presence of 2,4,5-trichloroaniline (100%).

EXAMPLE NO. 19

2,6-Dichlorobromobenzene (0.992 g), DMF (4. g) and sodium hydroxide (0.4 g) were introduced in order into a (100 ml) jacketed Teflon autoclave.

The autoclave was closed and the mixture was heated with stirring to 220° C. for 24 hours. The conversion was then 89%.

After treatment of the reaction medium, 0.43 g of the mixture of chloro-N,N-dimethylanilines was brought into contact with pyridine hydrochloride (5.2 g).

The mixture was heated to 190° C. for 60 minutes.

HPLC analysis of the mixture showed the presence of 2,6-dichloroaniline (43%) and of 2-bromo-3-chloro-aniline (57%).

EXAMPLE NO. 20

Pyridine hydrochloride (4.35 g, 37.7 mmol) was added to 2,6-dichloro-4-trifluoromethyl-N,N-dimethylaniline (0.86 g, 3.3 mmol).

The mixture was heated to 185° C. for 2 hours.

HPLC analysis then showed the presence of 2,6-dichloro-4trifluoromethylaniline (76 mol%).

EXAMPLE NO. 21

(Monodemethylation)

2,6-Dichloro-4-trifluoromethyl-N,N-dimethylaniline (0.86 g, 3.3 mmol) and pyridinium acetate (5 g) were introduced into a (100 ml) jacketed Teflon autoclave.

The autoclave was closed and the mixture was heated to 190° C. for 2 hours.

HPLC analysis showed the presence of 2,6-dichloro-4-trifluoromethyl-N-methylaniline (yld. 9 mol%).

EXAMPLE NO. 22 (comparative)

A mixture of 2,6-dichloro-4-trifluoromethyl-N,N-dimethylaniline (0.810 g) and dimethylamine hydrochloride (3.5 g) was heated for 1 hour to 180° C.

HPLC analysis of the mixture indicated the absence of conversion.

EXAMPLE NO. 23

A mixture of 2,6-dichloro-4-trifluoromethyl-N,N-dimethylaniline (0.745 g), pyridine hydrochloride (34 mg) and dimethylamine hydrochloride (3.24 g) was heated for 1 hour to 180° C.

HPLC analysis of the mixture showed a yield (20%) of 2,6-dichloro-4-trifluoromethylaniline which was three times as high as theory if the pyridine alone were active.

EXAMPLE NO. 24 (conventional technique)

A solution of 2,6-dichloro-4-trifluoromethyl-N,N-dimethylaniline (1 g) in aqueous hydrobromic acid (47%, 5 g) was brought to reflux for 5 hours.

HPLC analysis of the mixture showed an 89% conversion and a 55% yield of 2,6-dichloro-4-trifluoromethylaniline.

EXAMPLE NO. 25 (comparative)

The object was to demonstrate the failure of non-free-radical halogenation.

2-Chloro-6-nitro-N,N-dimethylaniline (0.802 g, 4 mmol) dissolved in chloroform (10 ml) was introduced into a 100-ml Teflon reactor. A solution of bromine (0.64 g, 4 mmol) in chloroform (20 ml) was added to this solution. The mixture was stirred at room temperature for 4 hours. Analysis of the reaction mixture showed that nothing other than the starting material was present. (Analytical technique: gas chromatography and mass spectroscopy)

EXAMPLE NO. 26 (comparative with U.S. Pat. No. 2,887,514)

It was sought to demonstrate the need for the presence of a base.

3,4-Dichloro-4-trifluoromethylbenzene (4.62 g, 21.4 mmol) and dimethylformamide (22 g, 14 molar equivalents) were introduced in order into a (100 ml) jacketed Teflon autoclave.

The autoclave was closed and the mixture was heated with stirring for 5 hours to 200° C.

Analysis of the reaction medium by gas chromatography indicated a 3% conversion for a 2% yield of dimethylanilines.

3,4-Dichloro-4-trifluoromethylbenzene (4.62 g, 21.4 mmol), dimethylformamide (22 g, 14 molar equivalents) and solid sodium hydroxide (0.856 g, 2.5 molar equivalents) were introduced in order into a (100 ml) jacketed Teflon autoclave.

The autoclave was closed and the mixture was heated with stirring for 5 hours of 200° C.

Analysis of the reaction medium by gas chromatography indicated a 95% conversion for an 80% yield of 2-chloro-4-trifluoromethylaniline.

EXAMPLE NO. 27 (Examples of regeneration of pyridinium compounds and recycling process)

Pyridine hydrochloride may be readily obtained by techniques which are known to a person skilled in the art, for example, treatment of pyridine with a stoichiometric amount of a 36% solution of hydrochloric acid in water followed by azeotropic distillation of the water with toluene.

Process 2,6-Dichloro-4-trifluoromethyldimethylaniline (1.72 g, 6.6 mmol) was heated to 180° C. for 1 hour in the presence of pyridine hydrochloride (8.7 g, 37.7 mmol). An assay of the reaction mass indicated a 100% conversion. The reaction medium was then cooled to 140° C., and orthoxylene (5 ml) was added with stirring. At the end of 2 minutes, stirring was stopped and a separation into two layers occurred. The upper phase was recovered. Analysis by gas chromatography showed the presence of 2,6 dichloro-4-trifluoromethylaniline (1.47 g, 97% yield).

The lower phase containing a mixture of methylpyridinium and pyridinium hydrochlorides was regenerated at 200° C. by the action of ammonia. The pyridine recovered by distillation may be recycled.

Although preferred embodiments of the invention are described herein in detail, it will be understood by those skilled in the art that variations may be made thereto without departing from the spirit of the invention or the scope of the appended claims.

I claim:

1. A process for dealkylating a deactivated aniline, which comprises reacting said aniline with ammonia or a primary or secondary amine in the presence of a catalytic amount of a pyridine salt.

2. The process according to claim 1, wherein said pyridine salt is a pyridine hydrohalide.

3. The process according to claim 2, wherein said pyridine salt is pyridine hydrochloride.

4. The process according to claim 1, wherein said amine has a pKa which is greater than that of said pyridine salt.

5. The process according to claim 4, wherein said amine has a pKa which is at least 2 units greater than that of said pyridine salt.

6. The process according to claim 1, wherein said reaction is performed at a temperature of between 150° C. and 250° C.

7. The process according to claim 6, wherein said reaction is performed at a temperature of between 180° C. and 220° C.

8. The process according to claim 1, wherein said amine is a mixture of amines.

9. The process according to claim 1, wherein said amine is pyridine or substituted pyridine.

10. The process according to claim 1, wherein said amine is an amine hydrohalide.

11. The process according to claim 1, wherein said amine is an amine hydrochloride.

12. The process according to claim 1, wherein said pyridine salt is a quinoline salt.

13. The process according to claim 1, wherein said pyridine salt is a mixture of pyridine salts.

14. The process according to claim 1, wherein an excess of between 1 and 50 equivalents of amine is used, relative to the stoibichiometry of dealkylation.

15. The process according to claim 1, wherein an excess of between 2 and 10 equivalents of amine is used, relative to fine stoichiometry of dealkylation.

16. The process according to claim 1, wherein an excess of amine and an excess of pyridine salt are used.

17. The process according to claim 1, wherein acid associated with the aniline has a pKa no greater than 5.

18. The process according to claim 1, wherein acid associated with the aniline has a pKa no greater than 1.

19. The process according to claim 1, wherein acid associated with the aniline has a pKa no greater than zero.

* * * * *